US009039629B2

(12) United States Patent
Zhou et al.

(10) Patent No.: US 9,039,629 B2
(45) Date of Patent: May 26, 2015

(54) CARBON DIOXIDE MONITORING SYSTEM (75) Inventors: Sophia Zhou, Camarillo, CA (US); Eric Helfenbein, Sunnyvale, CA (US); John Cadigan, Concord, MA (US); William Grube, Windham, NH (US); James Russell, Seattle, WA (US); Saeed Babaeizadeh, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 329 days.

(21) Appl. No.: 13/126,033

(22) PCT Filed: Oct. 27, 2009

(86) PCT No.: PCT/IB2009/054755
§ 371 (c)(1),
(2), (4) Date: Apr. 26, 2011

(87) PCT Pub. No.: WO2010/052608
PCT Pub. Date: May 14, 2010

(65) Prior Publication Data
US 2011/0201957 A1 Aug. 18, 2011

Related U.S. Application Data

(60) Provisional application No. 61/112,569, filed on Nov. 7, 2008.

(51) Int. Cl.
*A61B 5/08* (2006.01)
*A61B 5/083* (2006.01)
*A61M 16/00* (2006.01)
*A61M 16/04* (2006.01)
*A61N 1/39* (2006.01)

(52) U.S. Cl.
CPC ....... *A61B 5/0836* (2013.01); *A61B 2560/0431* (2013.01); *A61H 2230/205* (2013.01); *A61M 16/0051* (2013.01); *A61M 16/04* (2013.01); *A61M 2230/432* (2013.01); *A61N 1/3925* (2013.01); *A61M 16/0084* (2014.02)

(58) Field of Classification Search
CPC ................. A61B 5/0836; A61B 5/082; A61H 2230/205; A61M 16/0051; A61M 16/04; A61M 2230/432
USPC ................. 128/204.18–204.29; 600/529–543
See application file for complete search history.

(56) References Cited

U.S. PATENT DOCUMENTS

| 4,424,806 A * | 1/1984 | Newman et al. ................. 601/41 |
| 2004/0236240 A1* | 11/2004 | Kraus et al. .................... 600/529 |
| 2005/0113704 A1 | 5/2005 | Lawson et al. |

(Continued)

*Primary Examiner* — Navin Natnithithadha
*Assistant Examiner* — Eric Messersmith (57) ABSTRACT

A CO2 monitoring system (20) is described which is operable to monitor the CO2 content of respiratory gases during intubation, CPR, or ventilation treatment of a patient. The patient's respiratory gases are sensed for CO2 content (17) and characteristics of a CO2 waveform are detected (30), such as waveform baseline, waveform amplitude, waveform frequency, waveform slope, waveform rhythm, and waveform corners. One or more of the waveform characteristics are analyzed in consideration of the type of respiration treatment being performed to identify an abnormal respiratory condition. These abnormal conditions may include the intubation tube located in the esophagus, ineffective CPR, or an airway obstruction, for example. When an abnormal condition is identified (34) a visual or audible alarm (40) is issued to alert a caregiver to tend to the patient.

15 Claims, 6 Drawing Sheets

(56) References Cited

U.S. PATENT DOCUMENTS

| | | |
|---|---|---|
| 2007/0000494 A1 | 1/2007 | Banner et al. |
| 2007/0261698 A1 | 11/2007 | Palatnik |
| 2008/0178880 A1 | 7/2008 | Christopher et al. |
| 2009/0020127 A1 * | 1/2009 | Boone et al. ............. 128/207.14 |

* cited by examiner

CARBON DIOXIDE MONITORING SYSTEM

CROSS REFERENCE TO RELATED APPLICATIONS

This application claims the benefit of U.S. provisional application Ser. No. 61/112,569 filed Nov. 7, 2008, which is incorporated herein by reference.

This invention relates to medical carbon dioxide (CO2) monitoring systems and, in particular, to a CO2 monitoring system that can be used with patients undergoing intubation, cardiopulmonary resuscitation (CPR), or ventilation.

CO2 monitoring systems are usually found in hospital surgical suites and intensive care units to monitor a patient's respiration. Generally these systems are sophisticated and sizeable ventilation systems which monitor the oxygen intake and respiratory CO2 of a patient. However, there are other scenarios where CO2 monitoring is desirable. One is during intubation where air is being supplied to a patient by a hand-operation respiration device. Another is during the application of CPR to a patient stricken by cardiac arrest. A portable unit is desirable in such situations, such as the MRx defibrillator monitor produced by Philips Healthcare (Andover, Mass.), which may be used in a hospital but is portable and can be taken to the site of an accident or location of a stricken patient. It would be desirable for such a portable monitor to be capable of monitoring the CO2 expiration of a patient and interpreting the waveform implications in all of these situations.

In accordance with the principles of the present invention, a CO2 monitoring system is described which can be configured in a portable monitoring device and which can be used in the hospital or in ambulatory settings. The CO2 monitoring system can be set to provide CO2 monitoring and interpretation during intubation, CPR treatment, or ventilation. A CO2 sensor produces a signal which is a measure of the CO2 level of a patient's respiration. The CO2 signal is digitized and recorded by the CO2 monitor. The CO2 signal samples may be analyzed for noise content and the noise level reduced to produce a "clean" CO2 signal. The CO2 waveform is detected and various characteristics of the waveform are measured. The waveform and its characteristics are classified as to various respiratory conditions. If an adverse respiratory condition is found, the monitor may issue an audio or visual alarm and/or may issue a clinical advisory statement to guide a clinician in successful treatment of the patient.

Figure 1:
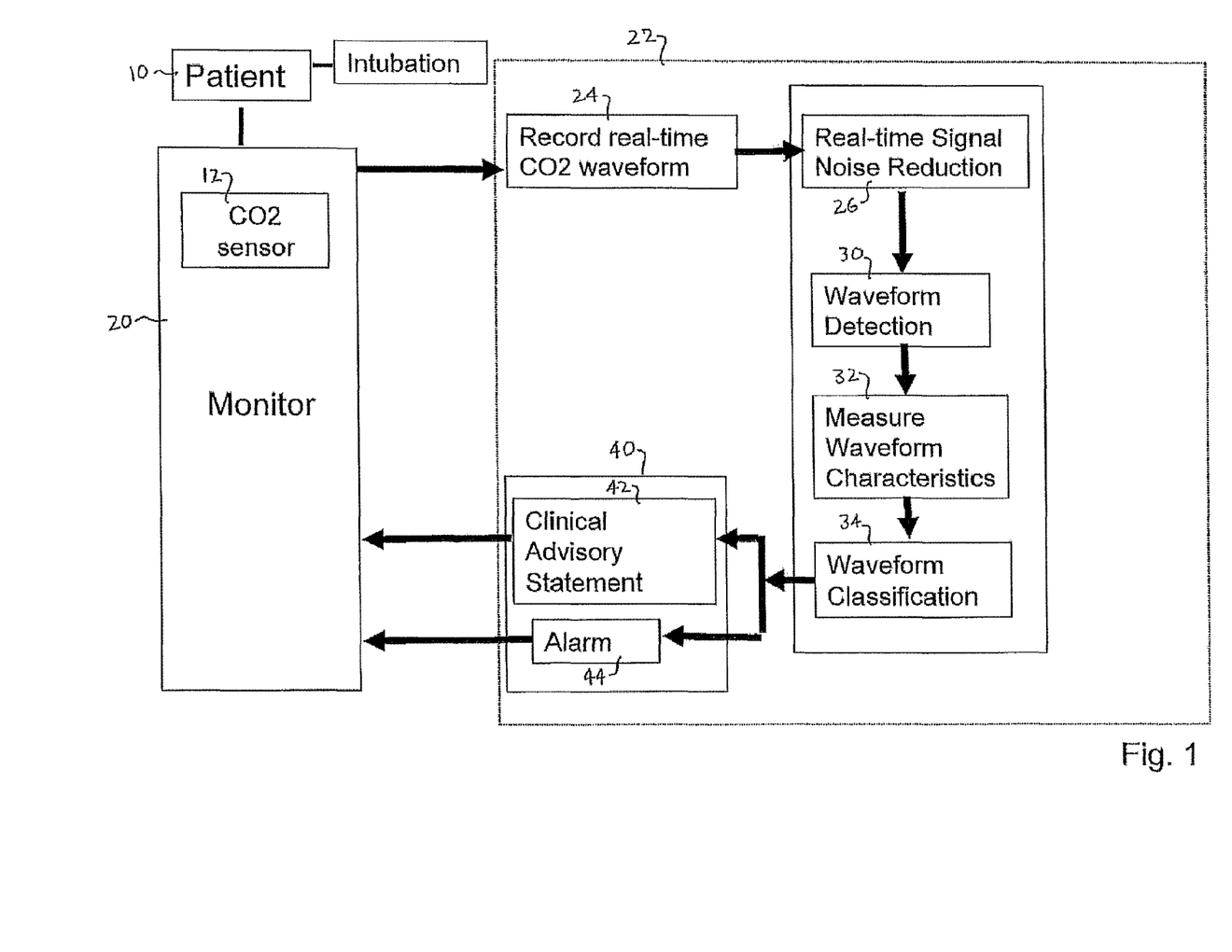
FIG. 1 illustrates in block diagram form a CO2 monitoring system of the present invention being used with a patient undergoing intubation.

Referring first to FIG. 1, a CO2 monitoring system 20 of the present invention is shown in block diagram form which is being used to monitor a patient 10 who is undergoing intubation. The respiratory gases of the patient are conducted to a CO2 sensor 12 of the monitor, which senses the CO2 content of the patient's expiration gases. The CO2 measurement signals from the sensor 12 are digitized into digital samples which are recorded as shown at 24 of the processing section 22 of the monitor 20. The CO2 signal samples are analyzed for noise content at 26 and may also undergo noise reduction. One technique for analyzing the noise content is to analyze the high frequency content of the signal samples. A clean CO2 signal will exhibit relatively little high frequency content. The noise level of the signals may be reduced by processing them with a digital low pass filter at 26 of the monitoring section 22. Acceptable CO2 signals then undergo waveform detection at 30. One technique for detecting the CO2 waveform is to take the difference of successive samples, which effectively detects the slope of the waveform. A normal CO2 waveform will exhibit a steeply rising slope as the patient begins to exhale, a relatively flat top during exhalation, and a steeply falling slope as exhalation ends and the patient draws another breath, as discussed more fully below. Certain characteristics of the detected waveform are then measured at 32. These characteristics may include the baseline of the waveform, the height or amplitude of the waveform, the frequency of the waveform, the rhythm of the waveform, the corners of the waveform, the slopes of the waveform, and characteristics of the shape of the waveform. The measured characteristics are then classified at 34 to assess whether the waveform exhibits the characteristics of normal respiration for the treatment being applied, or are characteristic of a particular difficulty which may be encountered during a particular treatment regimen. If a problem or difficulty is detected, an alarm 44 may be sounded or displayed to the clinician, or a clinical advisory statement 42 issued to advise the clinician that a particular problem or difficulty should be investigated.

When the CO2 monitoring system is coupled to the patient, it should be set to identify the treatment being applied to the patient, such as intubation, CPR, or ventilation. This may be done by a manual switch or input to the monitoring system which set by the clinician. The setting may also be done automatically by the particular treatment device being used. For instance, when the air conduit of an intubation device is connected to the monitor 20, the monitor may sense the connection of the air conduit and thereby is informed that intubation is being monitored. For CPR a CPR pad which is placed on the chest of the patient and depressed during CPR may be connected to the monitor and so inform the monitor that CPR is being performed. Another approach is to sense that the monitor is in the CPR mode to provide guidance to the rescuer administering CPR. During ventilation the ventilator or its air conduit may be connected to the monitor 20 to inform the monitor that ventilation is being performed. The identification of the treatment regimen will condition the monitor 20 to be particularly sensitive to respiratory conditions which may be expected during the treatment regimen being applied.

Figure 4:
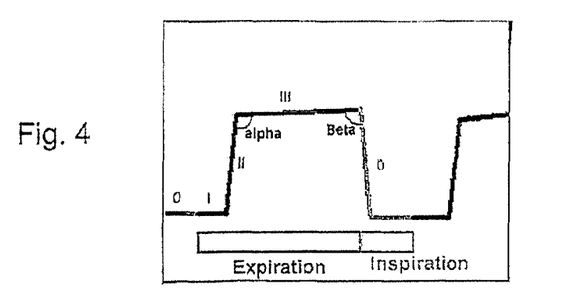
FIG. 4 illustrates standardized parameters of a CO2 waveform.
Figure 5:
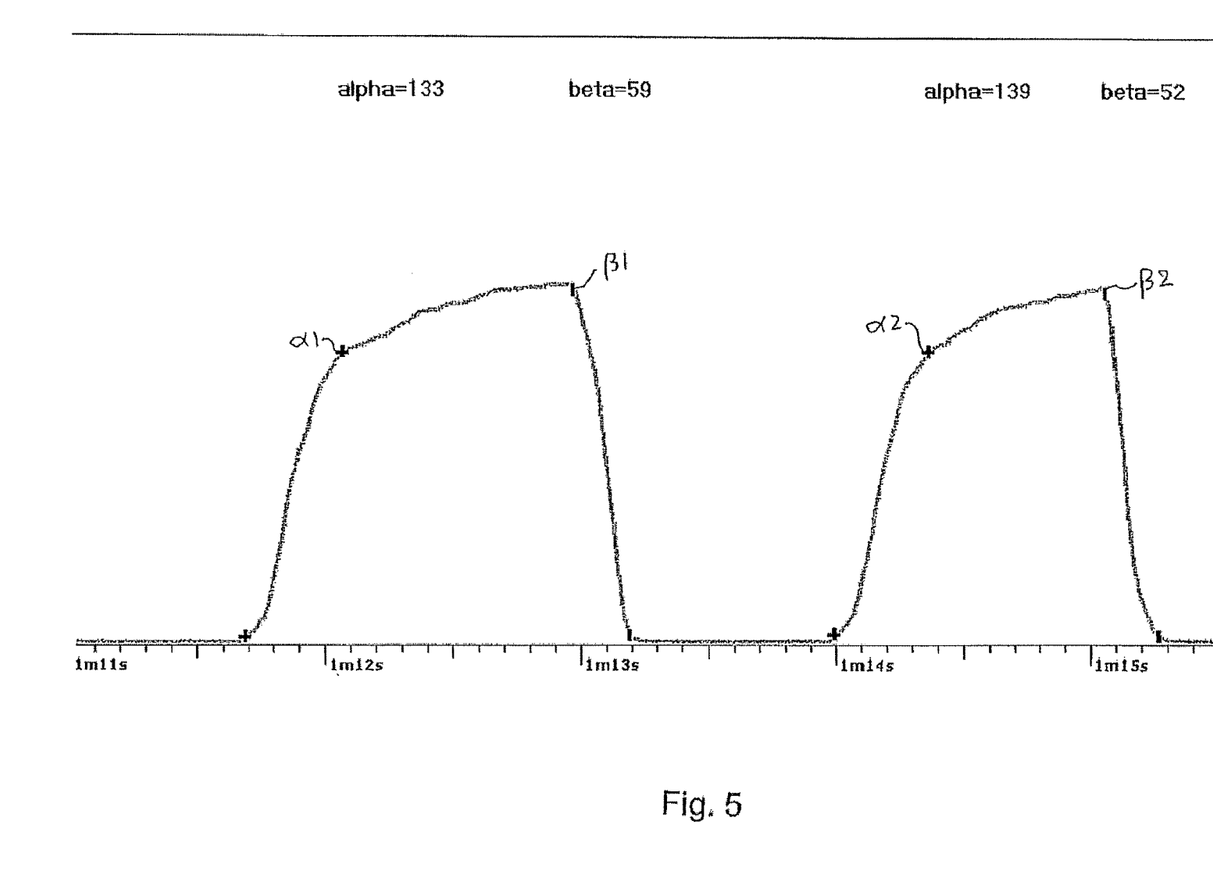
FIG. 5 illustrates a typical CO2 waveform sequence.

FIG. 4 illustrates the standard parameters of a normal CO2 waveform. When the patient exhales and the expiration phase begins, the waveform will rise from a baseline I with a steep slope II until a sustained level III of CO2 content of the exhaled air is attained. The waveform will exhibit a corner alpha when the sustained level is reached. When the patient finishes exhaling the waveform will drop from a corner beta at the start of the inspiration phase 0. The waveform will then repeat in this manner at the frequency and periodicity of the patient's respiration. An actual waveform trace is shown in FIG. 5 along a horizontal time scale. The waveform is seen to have alpha points α1 and α2 at inflection points during the initial rise of the waveform, and sharply defined beta points β1 and β2 at the onset of inspiration and the fall of the waveform. Other characteristics such as the maximum amplitude, average height, waveform duration, and waveform frequency are also apparent in this illustration.

Figure 6A:
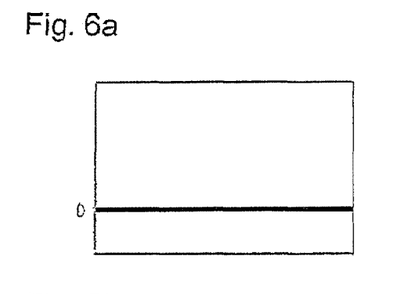
FIGS. 6a-6c Illustrate typical CO2 waveforms which may be produced from a patient undergoing intubation.

FIG. 6 shows some of the respiration waveform patterns which may be anticipated during intubation. One difficulty that may arise, particularly with individuals with little experience with intubation, is that the intubation tube is inserted into the esophagus instead of the patient's endotrachial passageway. In that case the CO2 waveform may be nonexistent or flat, as shown in FIG. 6a. Knowing that intubation is being performed and seeing a flat waveform, the monitor 20 may activate the alarm 44 to alert the medical specialist that no respiratory pattern has been detected. A clinical advisory statement may also be issued in visual or voice prompt form to advise the medical specialist to check that the intubation tube is inserted into the trachea and not the esophagus.

Figure 6B:
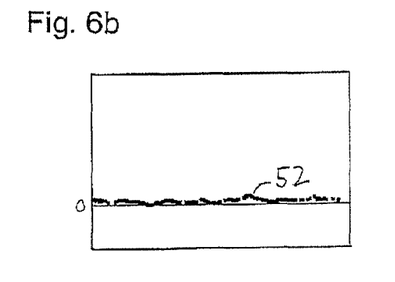

FIG. 6b illustrates another waveform that may be present when the intubation tube is inserted into the esophagus. The erratic but undefined waveform 52 is typical of that which may be present for a patient who has recently consumed a carbonated beverage. In that case it is the CO2 of the gastric system which is being detected, and not respiratory CO2. The same alarm and advisory may be issued by the monitor 20 as was issued in the previous example.

Figure 6C:
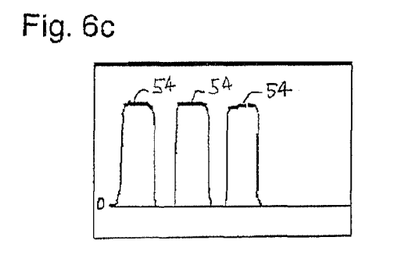

FIG. 6c illustrates the CO2 waveform that should be detected when the patient is properly intubated and is breathing with normal respiration cycles as shown by CO2 waveforms 54 in the illustration. The CO2 waveform produced by waveform detection is preferably displayed in real time on a display on the monitor 20.

Figure 2:
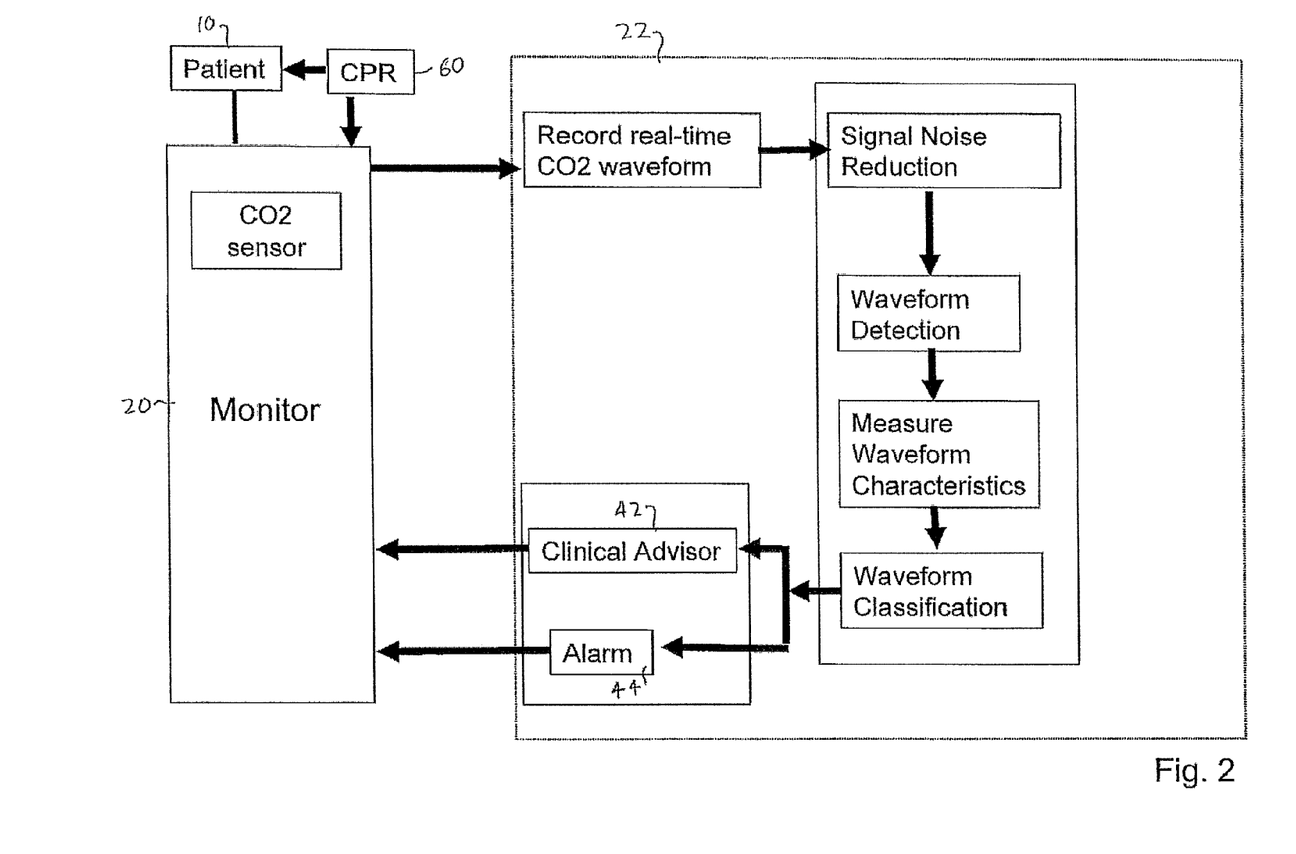
FIG. 2 illustrates in block diagram form a CO2 monitoring system of the present invention being used with a patient undergoing CPR.
Figure 7A:
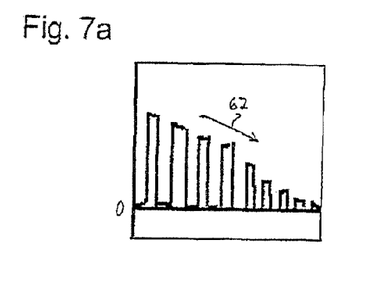
FIGS. 7a and 7b illustrate typical CO2 waveforms which may be produced from a patient undergoing CPR.
Figure 7B:
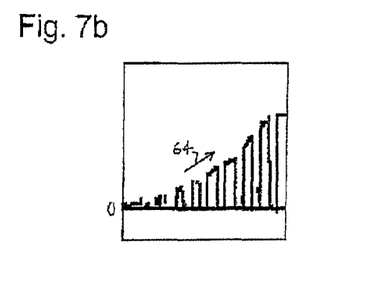

FIG. 2 illustrates the CO2 monitoring system of FIG. 1 when monitor 20 is being used with a patient who is undergoing CPR 60. FIGS. 7a and 7b illustrate waveforms which may be expected during application of CPR to a patient. CPR is performed by applying chest compressions at a rapid rate, generally about 100 compressions per minute. These rapid but firm compressions will cause the lungs to be compresses and recoil from compressions in short, high frequency increments as shown in these drawings. One characteristic of the CO2 waveforms that is significant during CPR is the trend of the CO2 waveforms. If the trend of the waveform amplitudes is downward as indicated by arrow 62 in FIG. 7a, it indicates that CO2 is being exchanged from the blood supply in ever decreasing amounts, and that the benefit of CPR is declining. In such case some other treatment regimen may be tried, such as assessing the ECG waveform for the possibility of ventricular fibrillation and, if identified, resuscitation by electrical defibrillation as may be done by the MRx defibrillator/monitor. However, if the trend of the waveform amplitudes is increasing as indicated by arrow 64 in FIG. 7b, this indicates that carbon dioxide is being removed from the blood stream in ever increasing amounts and that the patient is benefiting from the increased oxygenation of the blood supply. In the case of classification of the CO2 waveform trend as exhibiting the downward trend 62 of FIG. 7a, an alarm 44 may be issued by the monitor 20 or an advisory issued that the patient is not benefiting from CPR. If an upward trend 64 is identified as shown in FIG. 7b, the rescuer may be advised that the CO2 monitor has detected a positive benefit from CPR.

Figure 3:
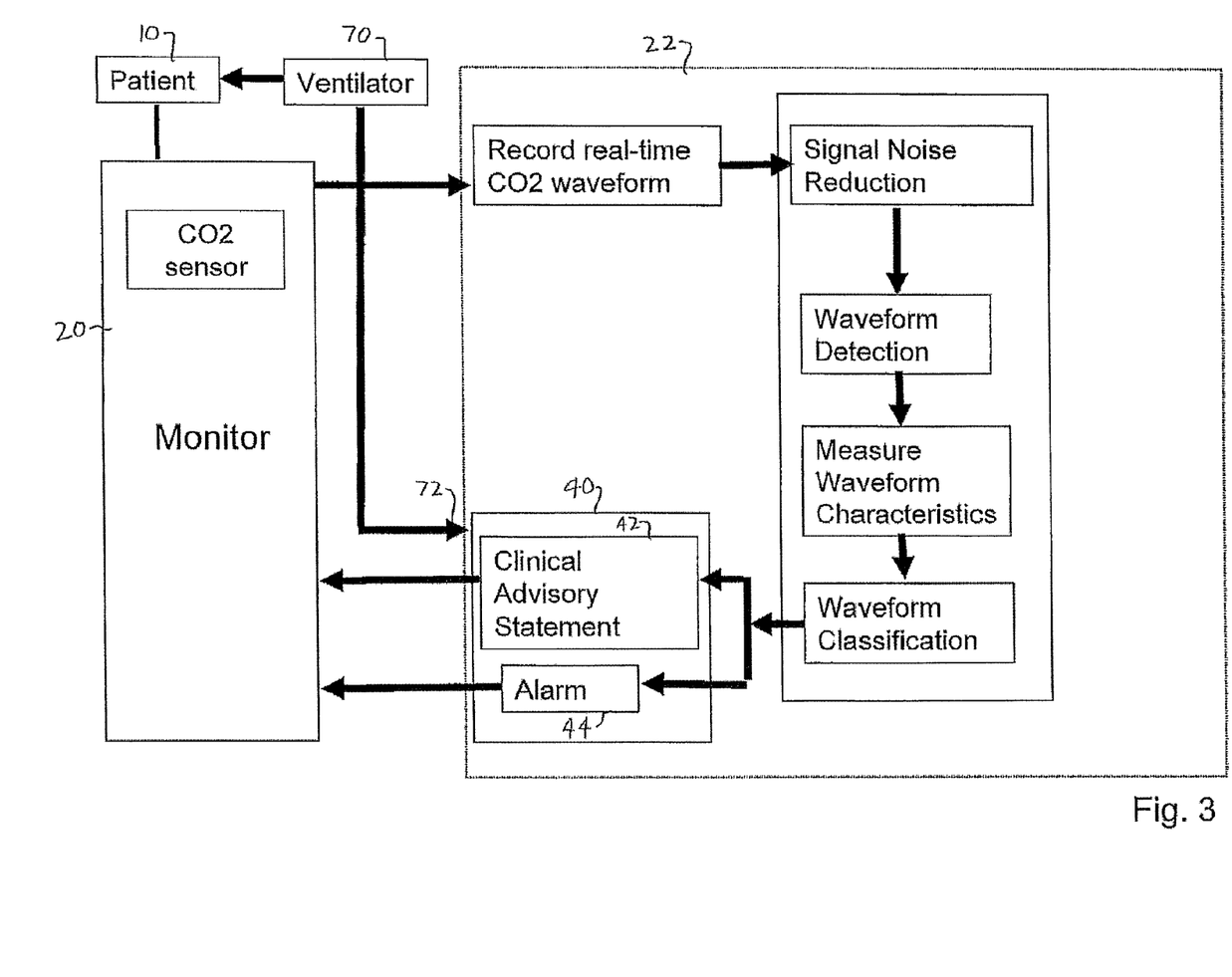
FIG. 3 illustrates in block diagram form a CO2 monitoring system of the present invention being used with a patient undergoing ventilation.
Figure 8A:
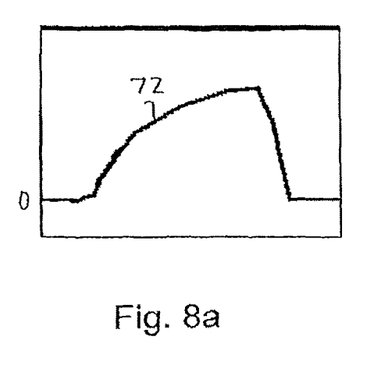
FIGS. 8a-8d illustrate typical CO2 waveforms which may be produced from a patient who is being ventilated.
Figure 8B:
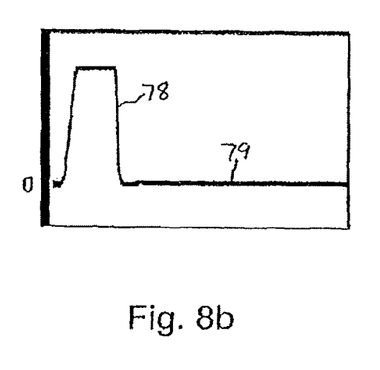

FIG. 3 illustrates a CO2 monitoring system of the present invention being used with a patient 10 who is undergoing ventilation. In this example the ventilator 70 is connected to the monitor as shown at 72 which indicates to the monitor that ventilation is being monitored. Other data useful in the classification of respiratory waveforms may also be provided to the monitor by this connection, such as the rate, pressure, oxygen levels, or other operating parameters or settings of the ventilator. FIG. 8 shows some of the CO2 waveforms which may be expected during ventilation of a patient. FIG. 8a illustrates a CO2 waveform 72 which does not rise sharply as exhalation begins. The waveform 72 does not exhibit a clearly defined alpha corner as illustrated in FIG. 5, for instance. This CO2 waveform 72 may be caused by an obstruction of the patient's airway. In this situation the monitor output 40 may issue an alarm 44 or an advisory 42 to advise medical personnel to check the patient's airway for obstruction. FIG. 8b illustrates a CO2 waveform pattern which may be produced when the patient experiences apnea and stops breathing. In that situation the regular pattern of CO2 waveforms 78 stops and only the flat baseline 79 is produced as no further CO2 waveforms are detected. An alarm 44 which may also be accompanied by an advisory are issued by the monitor 20 to alert medical personnel that the patient needs immediate attention.

Figure 8C:
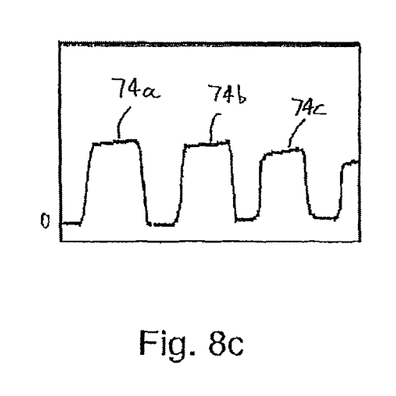
Figure 8D:
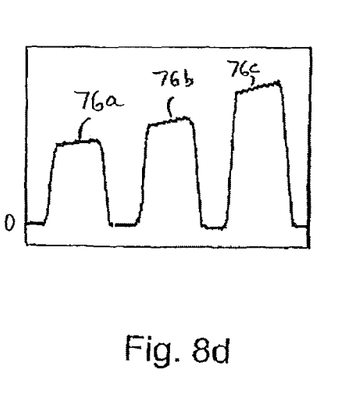

FIGS. 8c and 8d illustrate CO2 waveforms which may be produced to indicate that the ventilator settings need adjustment. In FIG. 8c the successive CO2 waveforms 74a, 74b, 74c are seen to exhibit continually decreasing amplitudes, indicating that less carbon dioxide is being expelled with each successive breath. This indicates a hyperventilation condition, where the patient is being ventilated at a rate which is excessively high and does not allow sufficient time for a full gas exchange with each breath. Medical personnel may then be alerted to reduce the rate of ventilation. In FIG. 8d the successive CO2 waveforms of increasing CO2 indicate a hypoventilation condition. The patient may be experiencing ventilation at too slow a rate, with a buildup of the CO2 content of the exchanged gases indicated with each breath. In this circumstance the medical personnel may be alerted to increase the rate of ventilation.

What is claimed is:

1. A carbon dioxide (CO2) monitoring system for use with patients undergoing intubation, cardiopulmonary resuscitation (CPR), or ventilation comprising:
   a CO2 sensor which receives respiratory gases from a patient and senses the CO2 content of the gases to produce CO2 measurement signals;
   a recorder which records samples of the CO2 measurement signals;
   a waveform detector responsive to the CO2 signal samples which identifies characteristics of a CO2 waveform;
   a monitor operable to identify which of an intubation mode, a CPR mode, and a ventilation mode is the use mode of the monitoring system;
   a waveform analyzer responsive to identified characteristics of the CO2 waveform and the use mode which analyzes the waveform characteristics in consideration of the use mode; and
   an alarm which produces an alarm output in response to the indication of an abnormal condition by the waveform analyzer.

2. The CO2 monitoring system of claim 1, wherein the samples of the CO2 measurement signals comprise digital signals.

3. The CO2 monitoring system of claim 2, wherein the identified characteristics of a CO2 waveform comprise at least one of waveform baseline, waveform amplitude, waveform frequency, waveform slope, waveform rhythm, and waveform corners.

4. The CO2 monitoring system of claim 3, wherein the monitor further comprises a manually settable user control which is operable to identify the use mode.

5. The CO2 monitoring system of claim 3, wherein the monitor is operable to identify the use mode by sensing a connection to a respiration treatment device used with a patient.

6. The CO2 monitoring system of claim 1, wherein the use mode is intubation, and further wherein the alarm is responsive to an abnormal condition comprising one of no respiration received or erratic CO2 waveform.

7. The CO2 monitoring system of claim 6, wherein the alarm output comprises a visual or audio advisory to check the intubation tube.

8. The CO2 monitoring system of claim 1, wherein the use mode is CPR, and further wherein the alarm is responsive to an abnormal condition comprising a downward trend of the CO2 waveform amplitude.

9. The CO2 monitoring system of claim 8, wherein the alarm output comprises a visual or audio advisory of the effectiveness of the CPR.

10. The CO2 monitoring system of claim 1, wherein the use mode is ventilation, and further wherein the alarm is responsive to an abnormal condition comprising one of airway obstruction, apnea, or undesirable rate of ventilation.

11. The CO2 monitoring system of claim 10, wherein the alarm output comprises one of check patient or adjust ventilator settings.

12. The CO2 monitoring system of claim 1, wherein the alarm is further operable to produce an output signal in response to normal respiration.

13. The CO2 monitoring system of claim 12, wherein the output signal produced during CPR comprises an indication that CPR is effective.

14. The CO2 monitoring system of claim 1, further comprising a display responsive to the waveform detector which displays a detected CO2 waveform in real time.

15. The CO2 monitoring system of claim 1, further comprising a noise analyzer which analyzes the noise content of CO2 signal samples.

* * * * *